United States Patent
Roy

(10) Patent No.: US 10,478,333 B2
(45) Date of Patent: Nov. 19, 2019

(54) OCULAR IONTOPHORESIS DEVICE

(71) Applicant: OPIA TECHNOLOGIES, Paris (FR)

(72) Inventor: Pierre Roy, Paris (FR)

(73) Assignee: OPIA TECHNOLOGIES (FR)

(*) Notice: Subject to any disclaimer, the term of this patent is extended or adjusted under 35 U.S.C. 154(b) by 454 days.

(21) Appl. No.: 15/114,640

(22) PCT Filed: Jan. 27, 2015

(86) PCT No.: PCT/EP2015/051613
§ 371 (c)(1),
(2) Date: Jul. 27, 2016

(87) PCT Pub. No.: WO2015/110660
PCT Pub. Date: Jul. 30, 2015

(65) Prior Publication Data
US 2016/0354239 A1 Dec. 8, 2016

(30) Foreign Application Priority Data
Jan. 27, 2014 (EP) .................................... 14290008

(51) Int. Cl.
*A61F 9/00* (2006.01)
*A61N 1/04* (2006.01)
(Continued)

(52) U.S. Cl.
CPC .......... *A61F 9/0017* (2013.01); *A61N 1/0428* (2013.01); *A61N 1/30* (2013.01); *A61N 1/325* (2013.01); *A61M 2210/0612* (2013.01)

(58) Field of Classification Search
CPC ........ A61F 9/0017; A61F 9/00; A61F 9/0008; A61F 9/0026; A61N 1/30; A61N 1/303;
(Continued)

(56) References Cited

U.S. PATENT DOCUMENTS 5,254,081 A 10/1993 Maurer et al.
6,154,671 A * 11/2000 Parel ..................... A61F 9/0017
604/20
(Continued)

FOREIGN PATENT DOCUMENTS

EP 0927560 A1 7/1999
FR 2869531 A1 11/2005
(Continued)

OTHER PUBLICATIONS

International Search Report for Application No. PCT/EP2015/051613 dated Mar. 27, 2015.
(Continued)

*Primary Examiner* — Bhisma Mehta
*Assistant Examiner* — William R Frehe
(74) *Attorney, Agent, or Firm* — Lerner, David, Littenberg, Krumholz & Mentlik, LLP

(57) ABSTRACT

The invention concerns an ocular iontophoresis device for delivering at least one active substance to an eyeball, comprising: a wall defining a tubular-shaped body delimitating laterally a reservoir configured for receiving the active substance(s), the wall comprising a circular distal end configured for being positioned on an ocular surface of the eyeball and surrounding the cornea and a part of the sclera of the eyeball, a first electrode configured to be positioned in front of the sclera, said first electrode being configured for delivering a first current density to the active substance(s) of the reservoir, the first electrode defining an annular-shaped first surface that is arranged in a peripheral part of the reservoir, a second electrode configured to be positioned in front of the cornea, said second electrode being configured for delivering a second current density to the active substance(s) of the reservoir, the second electrode defining a disk-shaped second surface that is arranged in a central part
(Continued)

of the reservoir, first and second electrodes being arranged concentrically to each other, and at least one controller for independently controlling said first and second electrodes.

20 Claims, 6 Drawing Sheets

(51) Int. Cl.
*A61N 1/30* (2006.01)
*A61N 1/32* (2006.01)

(58) Field of Classification Search
CPC ........ A61N 1/327; A61N 1/306; A61N 1/325; A61N 1/0428; A61N 1/0448; A61M 2210/0612
See application file for complete search history.

(56) References Cited

U.S. PATENT DOCUMENTS

| | | | | |
|---|---|---|---|---|
| 7,805,189 | B2* | 9/2010 | Stein | A61N 1/37241 607/2 |
| 2005/0245856 | A1* | 11/2005 | Roy | A61F 9/00 604/20 |
| 2006/0088515 | A1* | 4/2006 | Higuchi | A61K 9/0009 424/94.1 |
| 2007/0112295 | A1* | 5/2007 | Roy | A61F 9/0017 604/20 |
| 2007/0123814 | A1* | 5/2007 | Roy | A61N 1/0424 604/20 |
| 2009/0033863 | A1* | 2/2009 | Blum | A61F 2/14 351/159.34 |
| 2009/0209899 | A1* | 8/2009 | Unger | A61M 37/0092 604/20 |
| 2011/0275981 | A1* | 11/2011 | Singh | A61B 17/0231 604/20 |
| 2011/0301526 | A1* | 12/2011 | Moslemy | A61N 1/0444 604/20 |
| 2012/0078162 | A1* | 3/2012 | Gibson | A61N 1/0424 604/21 |
| 2012/0201800 | A1 | 8/2012 | Higuchi et al. | |
| 2012/0302972 | A1* | 11/2012 | Higuchi | A61F 9/0017 604/290 |
| 2015/0190278 | A1* | 7/2015 | Gooding | A61F 9/009 606/4 |

FOREIGN PATENT DOCUMENTS

| | | |
|---|---|---|
| WO | 2005115281 A2 | 12/2005 |
| WO | 2012162459 A1 | 11/2012 |

OTHER PUBLICATIONS

European Search Report for Application No. 14290008.3 dated May 2, 2014.

* cited by examiner

State of the art

OCULAR IONTOPHORESIS DEVICE

CROSS REFERENCE TO RELATED APPLICATIONS

The present application is a national phase entry under 35 U.S.C. § 371 of International Application No. PCT/EP2015/051613 filed Jan. 27, 2015, published in English, which claims priority from EP Patent Application No. 14290008.3 filed Jan. 27, 2014, all of which are incorporated herein by reference.

FIELD OF THE INVENTION

The present invention relates to an ocular iontophoresis device for delivering medications (into the eye).

The principle of ocular iontophoresis is applying an electric field to an electrolytic substance containing at least one medication, in order to transport the medication(s) into the body or the organ to be treated, via the biological membranes of the eye.

BACKGROUND OF THE INVENTION

The human eye is made up of three coats, enclosing three transparent structures.

The outermost layer is composed of the sclera and the cornea. The sclera, also known as the white of the eye, is an opaque and fibrous layer that protects the eye, while the cornea is the transparent front part of the eye that covers the iris, pupil and anterior chamber. The cornea, with the anterior chamber and lens, refracts light. Therefore, the sclera and the cornea have very different intrinsic properties.

The middle layer consists of the choroid, the ciliary body which is the thickened anterior portion of the choroid, and the iris. The iris is composed of circular muscle fibers that constrict the pupil and radial muscle fibers that dilate the pupil.

The innermost layer is the retina, which is mainly composed of the neural tissue including photoreceptor cells that receive and process incoming light.

Within these coats are the aqueous humour, the vitreous body, and the flexible lens. The aqueous humour is a clear fluid that is contained in two areas: the anterior chamber between the cornea and the iris, and the posterior chamber between the iris and the lens. The lens is suspended to the ciliary body by the suspensory ligament, made up of fine transparent fibers. The vitreous body is a clear jelly that is much larger than the aqueous humour present behind the lens, and the rest is bordered by the sclera, zonule, and lens. They are connected via the pupil.

Document WO 2005/115281 describes an ocular iontophoresis device for applying active substances to an eye. FIG. 1 shows such a device 200.

Such a device 200 comprises an active electrode 201, a reservoir 202, and at least one medication 203 stored in the reservoir 202, a passive electrode 204 enabling the electric circuit to be looped, and an electrical power supply 205 delivering DC to the electrodes 201 and 204.

The reservoir 202 is delimited laterally by a wall 206 defining a tubular-shaped body and comprising a distal end 207 configured for being positioned on an ocular surface 208 of the eye and surrounding the cornea 209 and a part of the sclera 210.

The device 200 is therefore adapted for treating the sclera 210 and the cornea 209 simultaneously.

However, as described above, the sclera and the cornea have very different intrinsic properties. In particular, the maximum tolerable current density for the cornea 209 is about 2 mA/cm$^2$, while the maximum tolerable current density for the sclera 210 is about 10 mA/cm$^2$. Furthermore, medication molecules having a size greater than 1.500 Da are not able to penetrate into the cornea 209, while medication molecules having a size lower than 150.000 Da are able to penetrate into the sclera 210.

Therefore, the intrinsic properties of the cornea 209 usually impose the medication and the current density to be applied by the active electrode 201 for treating simultaneously the cornea 209 and the sclera 210.

Therefore, there is a need for developing an ocular iontophoresis device configured for treating simultaneously the cornea and the sclera whilst taking into account intrinsic properties of each ocular tissue.

Document WO2012/162459 also describes an iontophoresis device of the state of the art. This device comprises a first chamber and a second chamber having annular shapes with the second chamber being inside the first chamber, so that first and second chambers form concentric rings. First and second chambers are further configured for receiving the medication(s). The first chamber and the second chamber are respectively connected to a first electrode and a second electrode configured for being in communication with the medication(s) received in the first and the second chambers, respectively. In this document, when the device is positioned on the eyeball of a patient, the first chamber surrounds the cornea of the eyeball, while the second chamber is between the first chamber and the cornea of the eyeball. Therefore, such a device is only configured for treating the sclera of the eyeball. As a result, this document is only dedicated to the treatment of the sclera and does not address the technical problem of treating simultaneously the cornea and the sclera whilst taking into account intrinsic properties of each ocular tissue.

Document US2012/0201800 describes another example of an iontophoresis device of the state of the art. This device comprises an outer ring electrode and an inner ring electrode, associated with an outer reservoir and an inner reservoir, respectively. In this document, the outer electrode and the inner electrode are configured for being positioned on the sclera surrounding the cornea, when the device is positioned on the eyeball of a patient. Therefore, such a device is only configured for treating the sclera of the eyeball. As a result, this document is only dedicated to the treatment of the sclera and does not address the technical problem of treating simultaneously the cornea and the sclera whilst taking into account intrinsic properties of each ocular tissue.

SUMMARY OF THE INVENTION

The present invention proposes an ocular iontophoresis device for delivering at least one active substance to an eyeball, comprising:
- a reservoir configured for receiving at least one active substance,
- a wall defining a tubular-shaped body arranged along a longitudinal axis, delimitating laterally the reservoir and comprising a circular distal end configured for being positioned on an ocular surface of the eyeball and surrounding the cornea and a part of the sclera of the eyeball,
- a first electrode configured to be positioned in front of the part of the sclera which is surrounded by the wall when the wall is in place on said ocular surface, said first electrode being configured for delivering a first current density to at least one active substance of the reservoir, the first electrode defining an annular-shaped first surface that is arranged over a peripheral part of the reservoir, a second electrode configured to be positioned in front of the cornea when the wall is in place on said ocular surface, said second electrode being configured for delivering a second current density to at least one active substance of the reservoir, the second electrode defining a disk-shaped second surface that is arranged over a central part of the reservoir, first and second electrodes are arranged concentrically to each other, so that the first electrode and the second electrode are respectively positioned in front of the sclera and in front of the cornea, when the device is positioned on said ocular surface, and at least one controller for independently controlling said first and second electrodes.

Preferably, a maximum external diameter of the first electrode is 22 mm, a maximum internal diameter of the first electrode is 12.5 mm, and a maximum diameter of the second electrode is 11.5 mm.

Preferably, the first current density is less than 10 mA/cm$^2$.

Preferably, the second current density is less than 2 mA/cm$^2$.

Preferably, first and second electrodes are configured for applying first and second density currents respectively during at most 10 min.

Preferably, a distance between first and second electrodes and the distal end of the wall defining the reservoir is greater than 4 mm.

According to one embodiment of the invention, the reservoir comprises a separating wall defining a first and a second chamber arranged concentrically to each other, the first chamber receiving the first electrode and the second chamber receiving the second electrode.

Preferably, a disk-shaped support surface extends at a proximal end of the separating wall for closing at least the second chamber, and wherein first and second electrodes are formed directly on the support surface by electroplating or by depositing an ink comprising an electrically conductive material using the technic of pad-printing.

Preferably, a disk-shaped support surface extends at a proximal end of the separating wall for closing at least the second chamber and comprises a suction opening leading to the second chamber for applying a vacuum on the cornea, when the device is positioned on said ocular surface.

Preferably, a disk-shaped support surface extends at a proximal end of the separating wall for closing the reservoir and includes a holding part arranged peripherally and cooperating with a supplementary holding part arranged at a proximal end of the wall defining the reservoir.

Preferably, the ocular iontophoresis device further comprises a grid arranged within the second chamber and configured for maintaining the elastic deformation of the cornea, when the device is positioned on said ocular surface.

According to another embodiment of the invention, the reservoir comprises a first and a second separating wall concentrically arranged to the wall defining the reservoir, and defining a suction ring arranged between a first chamber provided in a peripheral part of the reservoir and receiving the first electrode and a second chamber provided in a central part of the reservoir and receiving the second electrode.

Preferably, first and second separating walls further comprise proximal ends that are connected to each other via an annular proximal surface for closing the suction ring, said proximal surface including a suction opening leading to the suction ring, said suction opening being configured for applying a light vacuum on the ocular surface, when the device is positioned on the ocular surface, so that the device is immobilized while the eye is treated.

Preferably, the device further comprises a disk-shaped support surface positioned at a proximal end of first and second separating walls and receiving first and second electrodes.

More preferably, first and second electrodes are formed directly on the support surface by printing an ink comprising an electrically conductive material using the technic of pad-printing.

Alternatively, first and second electrodes are grid-shaped and positioned on the support surface.

Preferably, an annular protrusion extending radially to the second separating wall within the second chamber is provided for holding the second electrode.

Preferably, annular protrusions extending within the first chamber, radially to the first separating wall and an annular skirt arranged peripherally and perpendicularly to the support surface, are provided for holding the first electrode.

Preferably, the first electrode is annular-shaped, and the second electrode is spiral-shaped.

Preferably, the support surface comprises at least one first opening leading to the first chamber for filling the first chamber with at least one active substance.

Preferably, the support surface comprises at least one second opening leading to second chamber for filling the second chamber with at least one active substance.

The support surface comprises for example openings leading to the reservoir for evacuating gases generated during the iontophoresis.

The support surface is for example integral with first and second separating walls.

The support surface is for example provided with outer and inner walls extending perpendicularly to the support surface and defining together a groove aligned with the first chamber, while the inner wall defines a cavity aligned with the second chamber.

The support surface comprises for example two independent parts, a first part being positioned in front of the first chamber and receiving the first electrode, and a second part being positioned in front of the second chamber and receiving the second electrode.

BRIEF DESCRIPTION OF THE DRAWINGS

The above, and other objects, features and advantages of this invention, will be apparent in the following detailed description which is to be read in connection with the accompanying drawings wherein.

DETAILED DESCRIPTION OF THE INVENTION

In the description below, only the distinguishing features between the different embodiments of the invention will be developed. Therefore, common features or options between the different embodiments of the invention will not be repeated.

Figure 1:
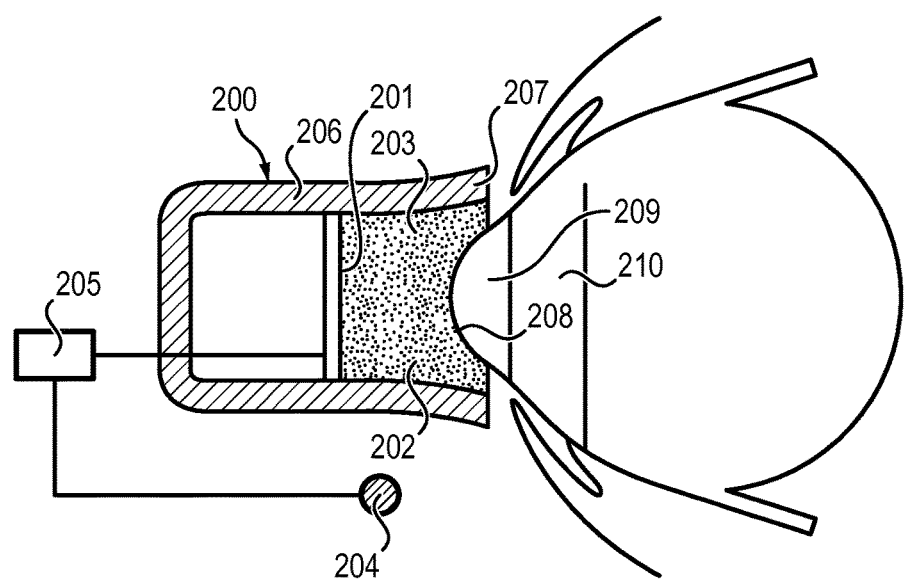
FIG. 1 (already described) shows a schematic view of an ocular iontophoresis device according to the state of the art.
Figure 2:
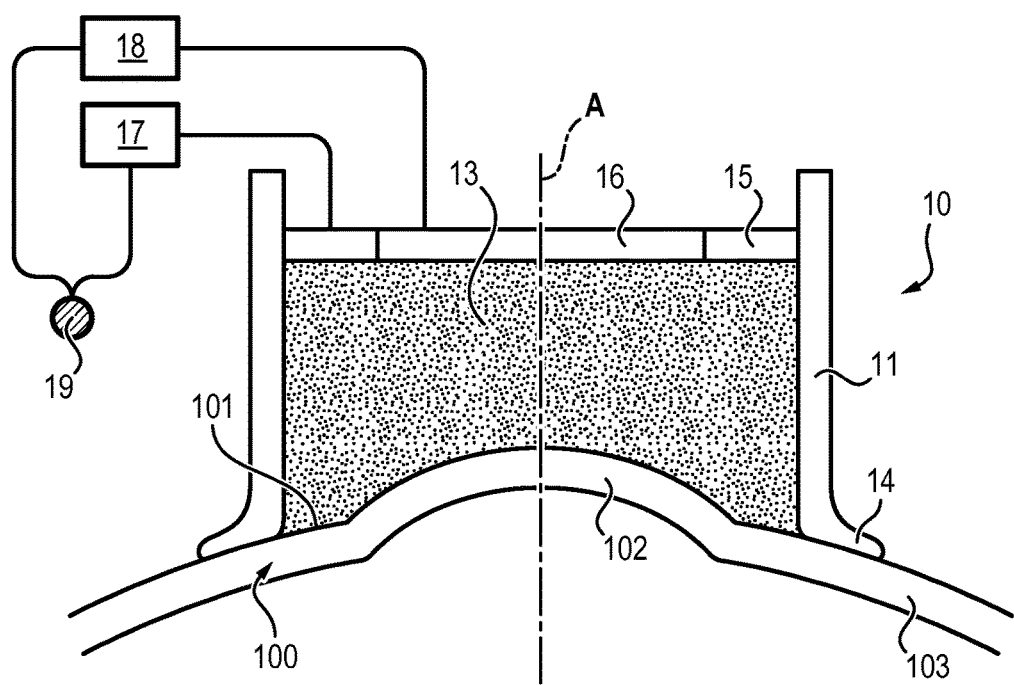
FIG. 2 shows a schematic view of an ocular iontophoresis device according to a first embodiment of the invention.

FIG. 2 shows an ocular iontophoresis device 10 for delivering active substances to an eyeball 100 according to one embodiment of the invention.

The device 10 comprises a wall 11 defining a tubular-shaped body arranged along a longitudinal axis A and delimitating laterally a reservoir 13 configured for receiving at least one active substance.

Active substances are defined here as any chemical compound used in the diagnosis, treatment, or prevention of disease or other abnormal condition. Active substances suitable for iontophoresis are for example antibiotic substances, antifungal substances, or anti-inflammatory substances.

More precisely, antibiotic substances suitable for iontophoresis are for example:

Vancomycin, positively charged, with a molecular weight of 1449;
Ceftazidime, negatively charged, with a molecular weight of 546;
Amikacin, positively charged, with a molecular weight of 585
Gentamycin, positively charged, with a molecular weight of 477;
Cefazolin, negatively charged, with a molecular weight of 454;
Ciprofloxacin, positively charged, with a molecular weight of 331;
Tobramycin, negatively charged, with a molecular weight of 467;
Ticarcillin, positively charged, with a molecular weight of 384;

Antifungal substances suitable for iontophoresis are for example:

Ketoconazole, positively charged, with a molecular weight of 531;
Miconazole, positively charged, with a molecular weight of 416;

Anti-inflammatory substances suitable for iontophoresis are for example:

Dexamethasone phosphate for IV administration, negatively charged, with a molecular weight of 516;
Methylprednisolone hemisuccinate IV, negatively charged, with a molecular weight of 474.

The body wall 11 comprises a circular distal end 14 configured for being positioned on an ocular surface 101 of the eyeball 100 and surrounding the cornea 102 and a part of the sclera 103. The part of the sclera 103 surrounded by the body wall 11 corresponds preferably to the pars plana.

The distal end 14 of the body wall 11 is also configured for deforming elastically when contacting with the ocular surface 101, so as to form an annular ring extending outwards with respect to the reservoir 13 that conforms to the shape of the ocular surface 101. Such an annular ring ensures therefore a good contact with the ocular surface 101.

The device 10 further comprises a first active electrode 15 arranged within the reservoir 13. The first electrode 15 is configured for being positioned in front of the part of the sclera 103 which is surrounded by the body wall 11, when the device 10 is positioned on the ocular surface 101. The first electrode 15 is further configured for delivering a first current density $D_1$ to at least one active substance of the reservoir 13.

The first electrode 15 preferably defines an annular-shaped surface arranged in a peripheral part of the reservoir 13, concentrically to the body wall 11. Therefore, when the device 10 is positioned on the ocular surface 101, the first electrode 15 is positioned in front of the part of the sclera 103 which is surrounded by the body wall 11, so that the first electrode 15 delivers the first current density $D_1$ to the active substance that penetrates into the sclera 103. The first electrode 15 is for example arranged along the body wall 11. The first electrode 15 has for example a maximum external diameter of 22 mm and a maximum internal diameter of 12.5 mm.

The device 10 also comprises a second active electrode 16 arranged within the reservoir 13. The second electrode 16 is configured for being positioned in front of the cornea 102, when the device 10 is positioned on the ocular surface 101. The second electrode 16 is further configured for delivering a second current density $D_2$ to at least one active substance. The second current density $D_2$ delivered by the second electrode 16 is preferably different from the first current density $D_1$ that is delivered by the first electrode 15.

The second electrode 16 preferably defines a disk-shaped surface arranged in a central part of the reservoir 13, concentrically to the first electrode 15 and the body wall 11. Therefore, when the device 10 is positioned on the ocular surface 101, the second electrode 16 is positioned in front of the cornea 102, so that the second electrode 16 delivers the second current density $D_2$ to the active substance that penetrates into the cornea. The second electrode 16 has a minimum diameter of 11.5 mm.

The device 10 further comprises controllers 17, 18 configured for independently controlling first and second electrodes 15, 16. Therefore, it is possible with the device 10 to treat simultaneously the cornea 102 and the sclera 103 whilst taking into account intrinsic properties of each ocular tissue 102, 103.

According to one embodiment of the invention, the cornea 102 and the sclera 103 are treated simultaneously. In other words, first and second electrodes 15, 16 are activated simultaneously, so as to deliver at the same time first and second current density $D_1$, $D_2$ to the active substances. According to another embodiment of the invention, the cornea 102 and the sclera 103 are treated sequentially. In other words, the first or the second electrode 15, 16 is first activated so as to deliver the first current density $D_1$ to the active substances, then, said first or second electrode 15, 16 is deactivated and the second or the first electrode 16, 15 is activated so as to deliver the second current density $D_2$ to the active substances.

The first electrode 15 is for example controlled by a first current generator 17 configured for delivering a first constant current intensity $I_1$ to the first electrode 15. The first current generator 17 is also connected to a passive electrode 19 configured for being positioned on the patient face, for example on the cheeks or preferably the forehead. The passive electrode 19 enables the electric circuit to be looped.

The passive electrode 19 is for example a transcutaneous electrical nerve stimulation type electrode.

The first electrode 15 defines a first surface $S_1$ extending perpendicularly to the longitudinal axis A. Therefore, the first current density $D_1$ delivered by the first electrode 15 is equal to $I_1/S_1$. Preferably, the first current density $D_1$ is less than 10 mA/cm², in order to prevent damage to the part of the sclera 103 which is surrounded by the body wall 11. As described above, the first surface $S_1$ is preferably annular-shaped.

Preferably, the first current generator 17 is configured for applying the first current intensity $I_1$ during at most 10 min, in order to preserve lachrymal film function of the eye and avoid excessive drying of the ocular surface 101. More preferably, the first current generator 17 is configured for applying the first current intensity $I_1$ during 3 to 10 min, in particular 5 min.

The second electrode 16 is for example controlled by a second current generator 18 configured for delivering a second constant current intensity $I_2$ to the second electrode 16. The second current generator 18 is also connected to the passive electrode 19.

The second electrode 16 defines a second surface $S_2$ extending perpendicularly to the longitudinal axis A. Therefore, the second current density $D_2$ delivered by the second electrode 16 is equal to $I_2/S_2$. Preferably, the second current density $D_2$ is less than 2 mA/cm², in order to prevent damage to the cornea 102. As described above, the second surface $S_2$ is preferably disk-shaped.

Preferably, the second current generator 18 is configured for applying the second current intensity $I_2$ during at most 10 min, in order to preserve lachrymal film function of the eye and avoid excessive drying if the ocular surface. More preferably, the second current generator 18 is configured for applying the second current intensity $I_2$ during 3 to 10 min, in particular 5 min.

Preferably, a distance along the longitudinal direction between first and second electrodes 15, 16 and the distal end 14 of the body wall 11 is greater than 4 mm, so that a distance along the longitudinal direction between first and second electrodes 15, 18 and the ocular surface 101 is greater than 4 mm.

First and second current generators 17, 18 can be replaced by a dual-channel iontophoresis generator such as DUPEL generator from EMPI, as described in document U.S. Pat. No. 5,254,081.

A protective layer is optionally formed on first and second electrodes 15, 16 so as to protect said first and second electrodes 15, 16 and/or to protect the active substances from metallic contaminants, as described in document FR 2 869 531.

The device 10 is preferably made of an electrically insulating material, such as polymer materials.

More preferably, the device 10 is made of transparent polymer materials for controlling the filling of the reservoir 13 with the active substances and ensuring that first and second electrodes 15, 16 are in contact with the active substances.

The distal end 14 of the body wall 11 is preferably made of substantially flexible polymer material, so that the distal end 14 cannot damage the ocular surface 101. Such a flexible material is for example an elastomer polymer of the polyurethane (PUR) type, polyether block amide (PEBA), silicone (SI), styrene-ethylene-butadiene-styrene (SEBS), or ethylene propylene diene monomer (EPDM) rubber.

Figure 3:
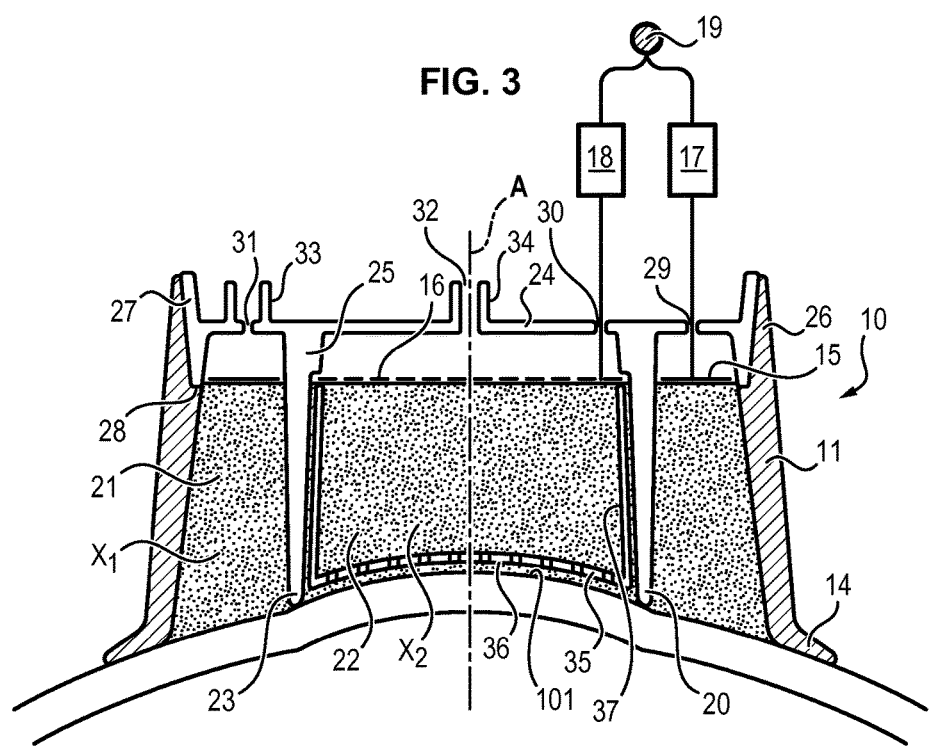
FIG. 3 shows a schematic view of an ocular iontophoresis device according to a second embodiment of the invention.

Now referring to FIG. 3, the reservoir 13 further comprises a separating wall 20 arranged concentrically to the body wall 11. The separating wall 20 defines a first chamber 21 arranged in the peripheral part of the reservoir 13 and receiving the first electrode 15, and a second chamber 22 arranged in the central part of the reservoir 13 and receiving the second electrode 16.

The separating wall 20 comprises a circular distal end 23 configured for being positioned on the ocular surface 101 and only surrounding the cornea 102. Therefore, the distal end 23 of the separating wall 20 separates the cornea 102 to the part of the sclera 103 surrounded by the body wall 11.

A dimension of the body wall 11 along the longitudinal direction is preferably greater that the dimension that is necessary for ensuring the contact of the distal end 23 of the separating wall 20 with the ocular surface 101, so that the distal end 14 of the body wall 11 can deform elastically and conform the shape of the ocular surface 101 when contacting the ocular surface 101.

A disk-shaped support surface 24 extending perpendicularly to the longitudinal axis A is provided at a proximal end 25 of the separating wall 20 for closing at least the second chamber 22. Preferably, the support surface 24 is provided for closing first and second chambers 21, 22.

The support surface 24 includes holding means 27 arranged peripherally and cooperating with supplementary holding means 28 arranged at a proximal end 26 of the body wall 11. For example, the support surface 24 comprises an annular skirt 27 arranged peripherally and extending along the longitudinal direction in both ways. The annular skirt 27 cooperates with a shoulder 28 arranged at the proximal end 26 of the body wall 11, and configured for stopping a translation of the support surface 24 along the longitudinal direction towards the distal end 14 of the body wall 11.

The annular skirt 27 is preferably made of substantially rigid polymer material. Such a rigid polymer material is for example polymethyl methacrylate (PMMA), polystyrene (PS), acrylonitrile-butadiene-styrene (ABS), polyethylene (PE), polypropylene (PP), polyamide (PA), polycarbonate (PC), or polyurethane (PUR).

The body wall 11 can be fitted to the annular skirt 27 of the support surface 24 using any suitable method, for example adhesive, heat sealing (e.g. by ultrasound, or by rotation, or by mirror), or by over-molding (also called insert-molding).

The annular skirt 27 can extend more or less towards the distal end 14 of the body wall 11 for adjusting the flexibility of the body wall 11. Such an adjustment ensures for example the elastic deformation of the distal end 14 of the body wall 11 when contacting the ocular surface 101, while operating mechanical reinforcement of the portion of the body wall 11 that cooperates with the annular skirt 27 and is subject to eyelid pressure.

First and second electrodes 15, 16 are for example formed directly on the support surface 24 by:
  electroplating;
  depositing an ink comprising an electrically conductive material using the technic of pad-printing;
  depositing a solid film, for example a solid film of acetate comprising an electrically conductive material;
  overmolding polymers comprising an electrically conductive material; or
  inserting metallic electrodes obtained by cutting, embossing, machining or progressive tooling. The electrodes 15, 16 are for example snapped on the support surface 24.

Preferably, first and second electrodes 15, 16 are provided on a face of the support surface 24 facing the separating wall 20, so that first and second electrodes 15, 16 are arranged in front of the ocular surface 101, when the device 10 is positioned on the ocular surface 101. Advantageously, openings 29, 30 leading to first and second chambers 21, 22, respectively, are provided in the support surface 24 for connecting first and second electrodes 15, 16 to first and second current generators 17, 18.

The support surface 24 further comprises at least one first opening 31 leading to the first chamber 21 for filling the first chamber 21 with at least one active substance, when the device 10 is positioned on the ocular surface 101.

The support surface 24 also comprises a second opening 32 leading to the second chamber 22. Preferably, the second opening 32 is arranged centrally to the support surface 24. The second opening 32 is configured for applying a light vacuum on the cornea 102, when the device 10 is positioned on the ocular surface 101, so that the device 10 is immobilized while the eye is treated. The second opening 32 is also configured for filling the second chamber 22 with active substances, when the device 10 is positioned on the ocular surface 101.

Preferably, first and second openings 31, 32 are respectively surrounded by protrusions 33, 34 extending from the support surface 24 along the longitudinal direction and towards the proximal end 26 of the body wall 11.

Therefore, as illustrated in FIG. 3, two different active substances $X_1$ and $X_2$ can be advantageously applied to the sclera 103 and the cornea 102, respectively. A first active substance $X_1$ is for example filled in the first chamber 21 for treating the sclera 103, while a second active substance $X_2$ is for example filled in the first chamber 22 for treating the cornea 102. Therefore, first and second active substances $X_1$ and $X_2$ can be adapted for each ocular tissue 102, 103. Therefore, a treatment adapted to each ocular tissue 102, 103 can be provided using the same device 10.

The device 10 can also include a disk-shaped grid 35 arranged within the second chamber 22. The grid 35 is configured for maintaining the elastic deformation of the cornea 102, when the device 10 is positioned on the ocular surface 101, and the light vacuum is applied on the cornea 102. The grid 35 comprises a concave surface 36 configured for fitting the convex shape of the cornea 102 and a wall 37 extending from the concave surface 36 along the longitudinal direction for facilitating the positioning of the grid 35 within the second chamber 22. The grid 35 is preferably made of a substantially rigid polymer material, such as a rigid polymer material is for example polymethyl methacrylate (PMMA), polystyrene (PS), acrylonitrile-butadiene-styrene (ABS), polyethylene (PE), polypropylene (PP), polyamide (PA), polycarbonate (PC), or polyurethane (PUR). According to this embodiment, the diameter of the disk-shaped second electrode 16 is maximal at 11.0 or 11.5 mm. The second electrode 16 therefore defines a second surface $S_2$ of 0.95 cm$^2$ or 1.51 cm$^2$, respectively. Further considering the thickness of the separating wall 20, the annular-shaped first electrode 15 will exhibit an internal diameter from 12.0 to 12.5 mm and an external diameter between 14.0 and 22.0 mm. The first electrode 15 defines therefore a first surface $S_1$ from 0.41 cm2 to 2.67 cm2. As a result, considering that the second current density $D_2$ cannot exceed 2 mA/cm$^2$ and that the first current density $D_1$ cannot exceed 10 mA/cm$^2$, the second current intensity $I_2$ applied to the second electrode 16 will be between 1.9 mA and 3.0 mA and the first current intensity $I_1$ applied to the first electrode 15 will be 26.7 mA for a maximum first surface $S_1$ of 2.67 cm2.

The support surface 24 and the proximal end 26 of the body wall 11, in particular the shoulder 28, are preferably made of a substantially rigid polymer material. Such a rigid polymer material is for example polymethyl methacrylate (PMMA), polystyrene (PS), acrylonitrile-butadiene-styrene (ABS), polyethylene (PE), polypropylene (PP), polyamide (PA), polycarbonate (PC), or polyurethane (PUR). The rigid portions 24, 26 of the device 10 can be made for example by machining, molding, vacuum casting, or any other method suitable for working such rigid polymer materials.

The rigid portions 24, 26 adds rigidity to the device 10, so as to avoid deformations of the device 10 under mechanical constraints, for example when the eyelid presses on the body wall 11 or when the light vacuum is applied within the second chamber 22.

On the contrary, distal ends 14, 23 of the body wall 11 and the separating wall 20 are preferably made of substantially flexible polymer material, so that distal ends 14, 23 cannot damage the ocular surface 101. Such a flexible material is for example an elastomer polymer of the polyurethane (PUR) type, polyether block amide (PEBA), silicone (SI), styrene-ethylene-butadiene-styrene (SEBS), or ethylene propylene diene monomer (EPDM) rubber.

Figure 4:
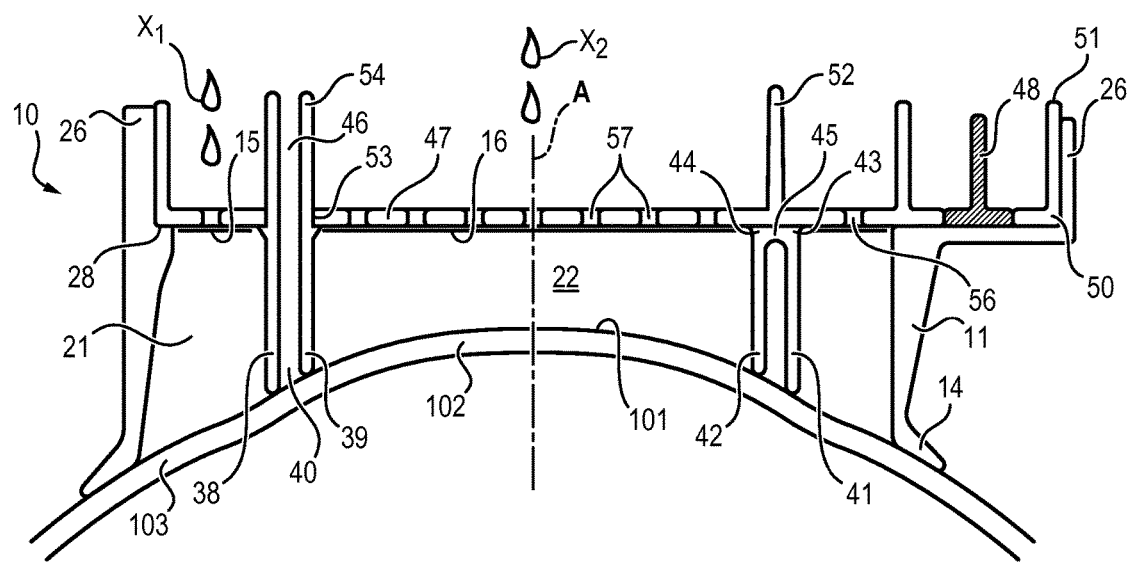
FIG. 4 shows a schematic view of an ocular iontophoresis device according to a third embodiment of the invention.

Now referring to FIG. 4, the reservoir 13 comprises first and second separating walls 38, 39 concentrically arranged to the body wall 11. First and second separating walls 38, 39 define a suction ring 40 arranged between a first chamber 21 provided in the peripheral part of the reservoir 13 and receiving the first electrode 15, and a second chamber 22 provided in the central part of the reservoir 13 and receiving the second electrode 16.

Each of first and second separating walls 38, 39 comprises a circular distal end 41, 42 configured for being positioned on the ocular surface 101. The distal end 41 of the first separating wall 38 is configured for surrounding a part of the sclera 103 and the cornea 102 or for only surrounding the cornea 102. The distal end 42 of the second separating wall 39 is configured for only surrounding the cornea 102.

A dimension of the body wall 11 along the longitudinal direction is preferably greater that the dimension that is necessary for ensuring the contact of distal ends 41, 42 of first and second separating walls 38, 39 with the ocular surface 101, so that the distal end 14 of the body wall 11 can deform elastically and conform the shape of the ocular surface 101 when contacting the ocular surface 101.

First and second separating walls 38, 39 further comprise proximal ends 43, 44 that are connected to each other via an annular proximal surface 45 for closing the suction ring 40. The proximal surface 45 preferably extends radially beyond first and second separating wall 38, 39.

The annular proximal surface 45 includes a suction opening 46 leading to the suction ring 40. The suction opening 46 is configured for applying a light vacuum on the ocular surface 101, when the device 10 is positioned on the ocular surface 101, so that the device 10 is immobilized while the eye is treated.

The device 10 is also provided with a disk-shaped support surface 47 positioned on the proximal surface 45 and receiving first and second electrodes 15, 16. First and second electrodes 15, 16 are preferably arranged on a first face of the support surface 47 positioned in front of the proximal surface 45.

Figure 5:
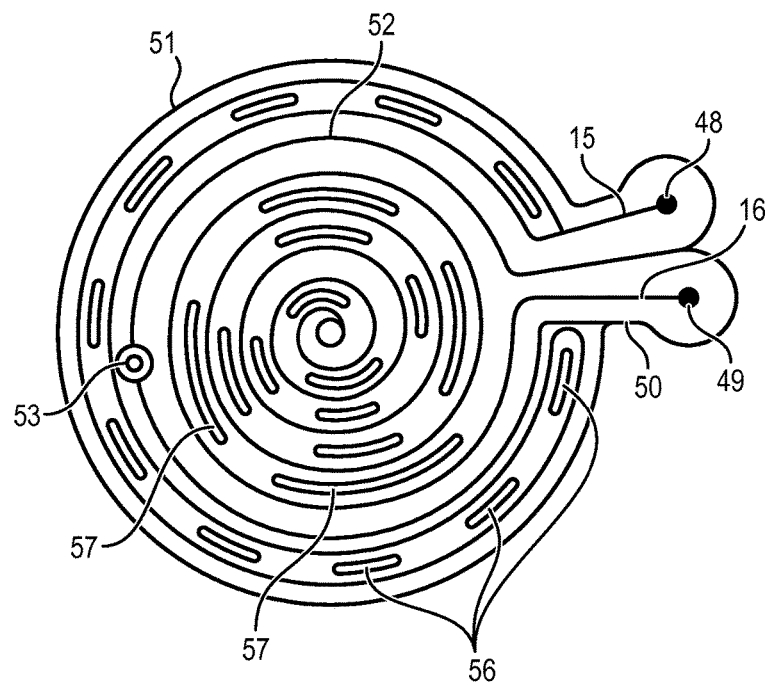
FIG. 5 shows a top view of a support surface of the ocular iontophoresis device illustrated in FIG. 4.

As shown in FIG. 5, first and second electrodes 15, 16 are for example formed directly on the support surface 47 by printing an ink comprising an electrically conductive material using the technic of pad-printing. The first electrode 15 is for example annular-shaped, while the second electrode 16 is for example spiral-shaped.

First and second electrodes 15, 16 are for example connected to first and second current generators 17, 18, respectively, by means of first and second connecting pins 48, 49 arranged in a tongue 50 extending from the peripheral part of the support surface 47, perpendicularly to the longitudinal axis A.

The support surface 47 is provided with an outer wall 51 extending perpendicularly to and surrounding a second face of the support surface 47.

The outer wall 51 is preferably made of substantially rigid polymer material such as for example polymethyl methacrylate (PMMA), polystyrene (PS), acrylonitrile-butadiene-styrene (ABS), polyethylene (PE), polypropylene (PP), polyamide (PA), polycarbonate (PC), or polyurethane (PUR).

The support surface 47 is also provided with an inner wall 52 extending perpendicularly to the second face and concentrically to the outer wall 51. Outer and inner walls 51, 52 define together a groove aligned with the first chamber 21, while the inner wall 52 defines a cavity that is aligned with the second chamber 22.

An opening 53 is arranged within the inner wall 52 of the support surface 47 and is configured to be coaxially arranged with the suction opening 46, when the support surface 47 is positioned on the proximal surface 45. The suction opening 46 is for example surrounded by a wall 54 extending from the proximal surface 45 along first and second separating walls 38, 39, and configured for being inserted in the opening 53.

Figure 6:
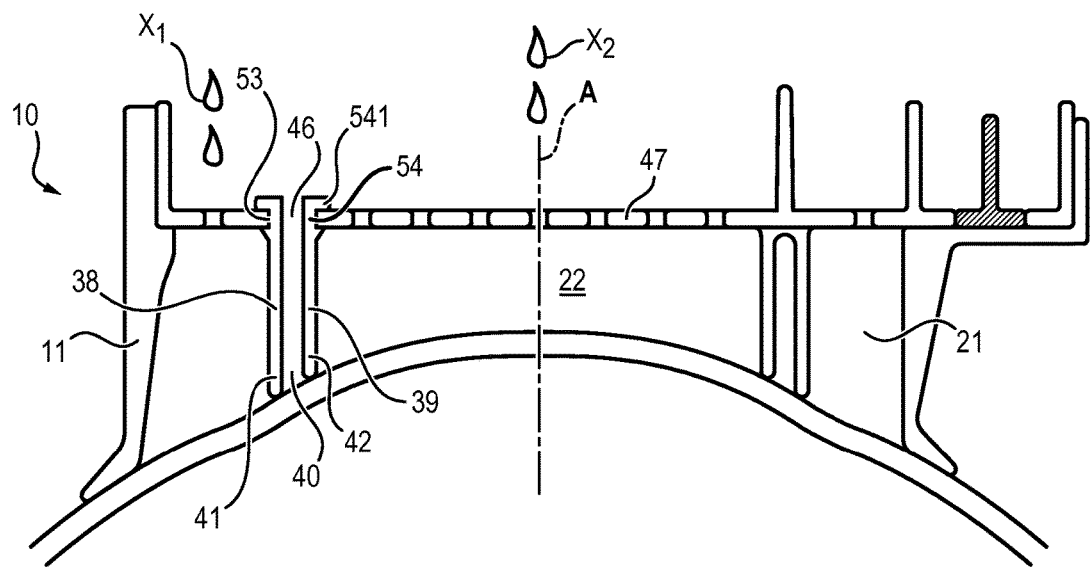
FIG. 6 shows a schematic view of an ocular iontophoresis device according to a fourth embodiment of the invention.

According to another embodiment of the invention illustrated in FIG. 6, the wall 54 extending from the proximal surface 45 and surrounding the suction opening 46 comprises at a proximal end an annular flange 541 extending radially towards the body wall 11, so that the wall 54 is snapped into the corresponding opening 53 of the support surface 47. The wall 54 can further be glued, or ultrasound welded.

The support surface 47 further comprises first openings 56 arranged between outer and inner walls 51, 52 and leading to the first chamber 21 for filling the first chamber 21 with at least one active substance. First openings 56 are also used to evacuate gases generated during the iontophoresis within the first chamber 21. Those gases are for example hydrogen at the cathode, and oxygen at the anode.

The support surface 47 also comprises second openings 57 arranged in the part of support surface 47 surrounded by the inner wall 52 and leading to the second chamber 22 for filling the second chamber 22 with at least one active substance. The second openings 57 are for example concentrically provided between each turn of the spiral-shaped second electrode 16. Second openings 57 are also used to evacuate gases generated during the iontophoresis within the second chamber 22.

Therefore, as illustrated in FIG. 4, two different active substances $X_1$ and $X_2$ can be advantageously applied to the sclera 103 and the cornea 102, respectively. A first active substance $X_1$ is for example filled in the first chamber 21 for treating the sclera 103, while a second active substance $X_2$ is for example filled in the first chamber 22 for treating the cornea 102. First and second active substances $X_1$ and $X_2$ can therefore be adapted for each ocular tissue 102, 103. Therefore, it is possible with the device 10 to treat simultaneously the cornea 102 and the sclera 103 whilst taking into account intrinsic properties of each ocular tissue 102, 103.

The proximal end 26 of the body wall 11 is for example provided with a shoulder 28 configured for receiving the peripheral part of the support surface 47, in particular the outer wall 51 and the tongue 50, and blocking a translation of the support surface 47 along the longitudinal direction towards the distal end 14 of the body wall 11. The outer wall 51 can be fitted to the body wall 11 using any suitable method, for example adhesive, heat sealing (e.g. by ultrasound, or by rotation, or by mirror), or by over-molding (also called insert-molding).

According to this embodiment, the diameter of the disk-shaped second electrode 16 is maximal at 9.0 mm. The second electrode 16 therefore defines a second surface $S_2$ of 0.64 cm$^2$. Further considering a thickness of first and second separating walls 38, 39 around 0.5 mm and a thickness of the suction ring 40 around 0.5 mm, the annular-shaped first electrode 15 will exhibit an internal diameter from 12.0 to 14.0 mm and an external diameter between 14.0 and 22.0 mm. The first electrode 15 defines therefore a first surface $S_1$ from 0.41 cm2 to 2.67 cm2. As a result, considering that the second current density $D_2$ cannot exceed 2 mA/cm$^2$ and that the first current density $D_1$ cannot exceed 10 mA/cm$^2$, the second current intensity $I_2$ applied to the second electrode 16 will be between 1.3 mA and the first current intensity $I_1$ applied to the first electrode 15 will be 26.7 mA for a maximum first surface $S_1$ of 2.67 cm2.

The support surface 47 and the proximal end 26 of the body wall 11, in particular the shoulder 28, are preferably made of a substantially rigid polymer material. Such a rigid polymer material is for example polymethyl methacrylate (PMMA), polystyrene (PS), acrylonitrile-butadiene-styrene (ABS), polyethylene (PE), polypropylene (PP), polyamide (PA), polycarbonate (PC), or polyurethane (PUR). The rigid portions 47, 26 of the device 10 can be made for example by machining, molding, vacuum casting, or any other method suitable for working such rigid polymer materials.

The rigid portions 47, 26 adds rigidity to the device 10, so as to avoid that the device 10 deforms, when the eyelid apply a pressure on the body wall 11 or when the light vacuum is applied within suction ring 40.

On the contrary, distal ends 14, 41, 42 of the body wall 11 and first and second separating walls 38, 39 are preferably made of substantially flexible polymer material, so that distal ends 14, 41, 42 cannot damage the ocular surface 101. Such a flexible material is for example an elastomer polymer of the polyurethane (PUR) type, polyether block amide (PEBA), silicone (SI), styrene-ethylene-butadiene-styrene (SEBS), or ethylene propylene diene monomer (EPDM) rubber.

Figure 7:
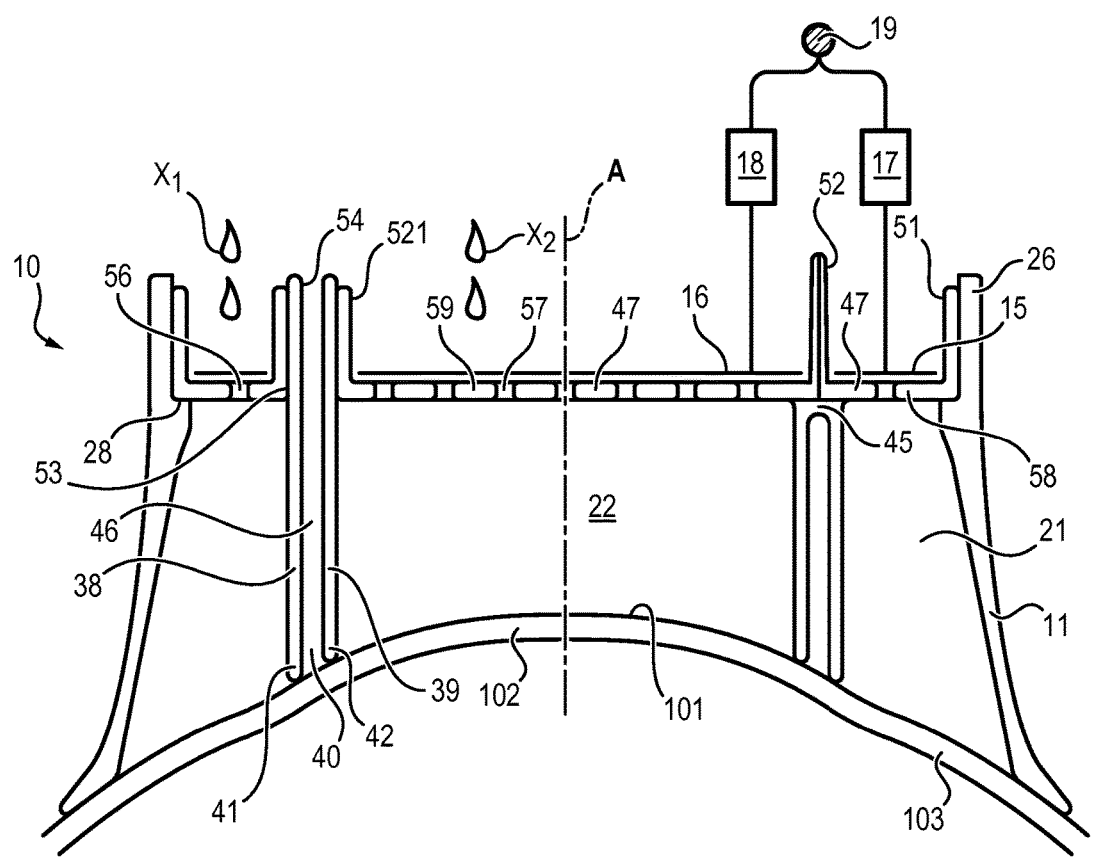
FIG. 7 shows a schematic view of an ocular iontophoresis device according to a fifth embodiment of the invention.

FIG. 7 shows another embodiment of the device 10 wherein the support surface 47 comprises two parts 58, 59 that are not integral with each other.

The first part 58 defines an annular-shaped surface configured for receiving the first electrode 15 and being positioned in front of the first chamber 21. The first part 58 is positioned on the proximal surface 45 on the one hand, and on the other, on the shoulder 28 arranged at the proximal end 26 of the body wall 11. The first part 58 further comprises outer and inner walls 51, 52 extending peripherally to the first part 58, along the longitudinal direction and towards the proximal end 26 of the body wall 11. Outer and inner walls 51, 52 define together a groove aligned with the first chamber 21.

The second part 59 defines a disk-shaped surface configured for receiving the second electrode 16 and being positioned in front of the second chamber 22. The second part 59 is positioned on the proximal surface 45. The second part 59 further comprises an outer wall 521 extending peripherally to the second part 59, along the longitudinal direction and towards the proximal end 26 of the body wall 11. The inner wall 52 of the first part 58 and the outer wall 521 of the second part 59 contact for example each other.

According to this embodiment, first and second electrodes 15, 16 are for example grid-shaped and positioned on the second face of the support surface 47, so that there is no need for fixing the electrodes 15, 16 to the support surface 47.

This embodiment is however also applicable to the support surface 47 illustrated in FIG. 5.

Each of the inner wall 52 of the first part 58 and the outer wall 521 of the second part 59 preferably comprises a concavity that conforms the shape of the wall 54 extending from the proximal surface 45 and surrounding the suction opening 46. Said concavities form therefore together the opening 53 of the support surface 47 that receives the wall 54 surrounding the suction opening 46.

The first part 58 further comprises first openings 56 leading to the first chamber 21 for filling the first chamber 21 with at least one active substance and the second part 59 further comprises second openings 57 leading to the second chamber 22 for filling the second chamber 22 with at least one active substance. First and second openings 56, 57 are also used to evacuate gases generated during the iontophoresis within first and second chambers 21, 22, respectively.

Therefore, as illustrated in FIG. 7, two different active substances $X_1$ and $X_2$ can be advantageously applied to the sclera 103 and the cornea 102, respectively. A first active substance $X_1$ is for example filled in the first chamber 21 for treating the sclera 103, while a second active substance $X_2$ is for example filled in the first chamber 22 for treating the cornea 102. First and second active substances $X_1$ and $X_2$ can therefore be adapted for each ocular tissue 102, 103. Therefore, it is possible with the device 10 to treat simultaneously the cornea 102 and the sclera 103 whilst taking into account intrinsic properties of each ocular tissue 102, 103.

Figure 8:
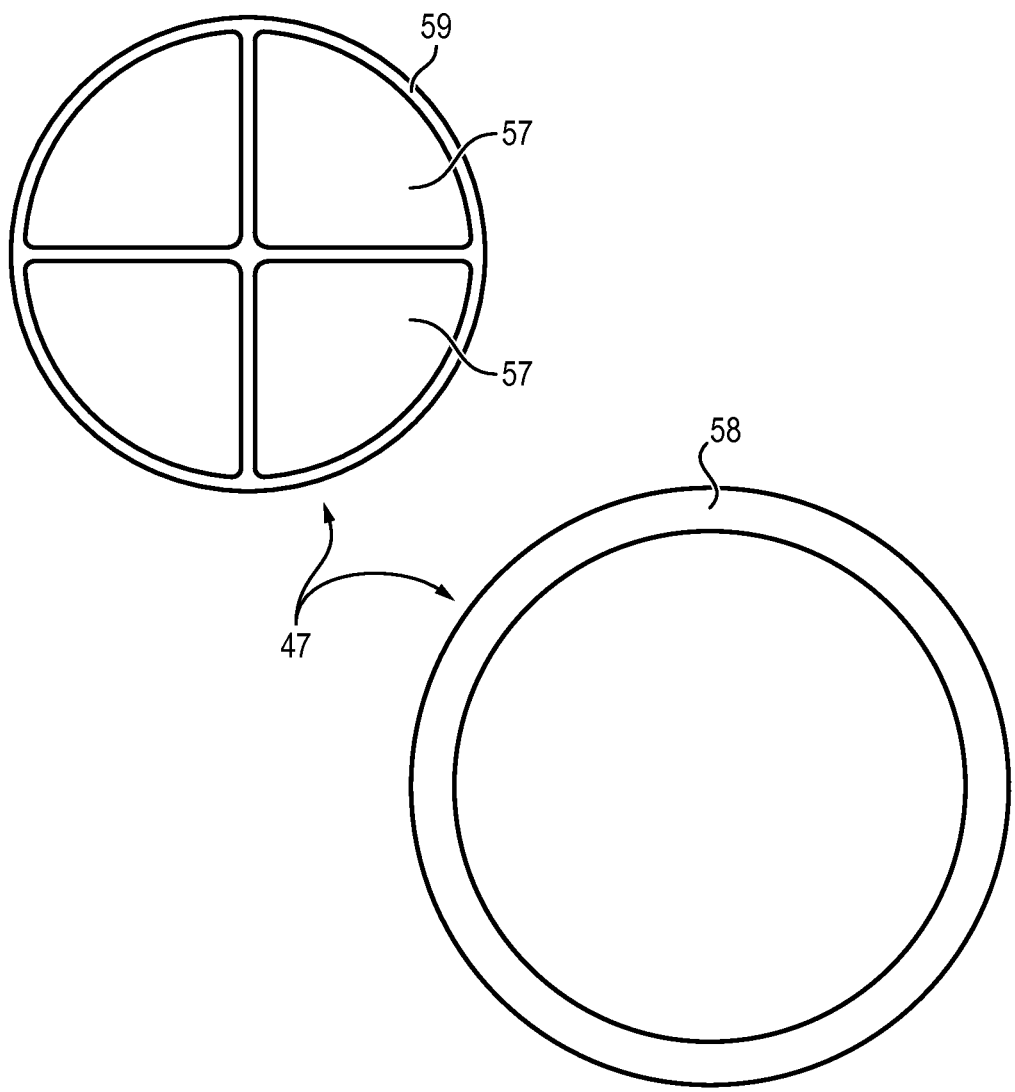
FIG. 8 shows a top view of a support surface of an ocular iontophoresis device according to another embodiment of the invention.

As illustrated in FIG. 8, the second part 59 can comprise a ring provided with the outer wall 521 and two diameters crossing each other. The ring and the diameters define together second openings 57.

Figure 9:
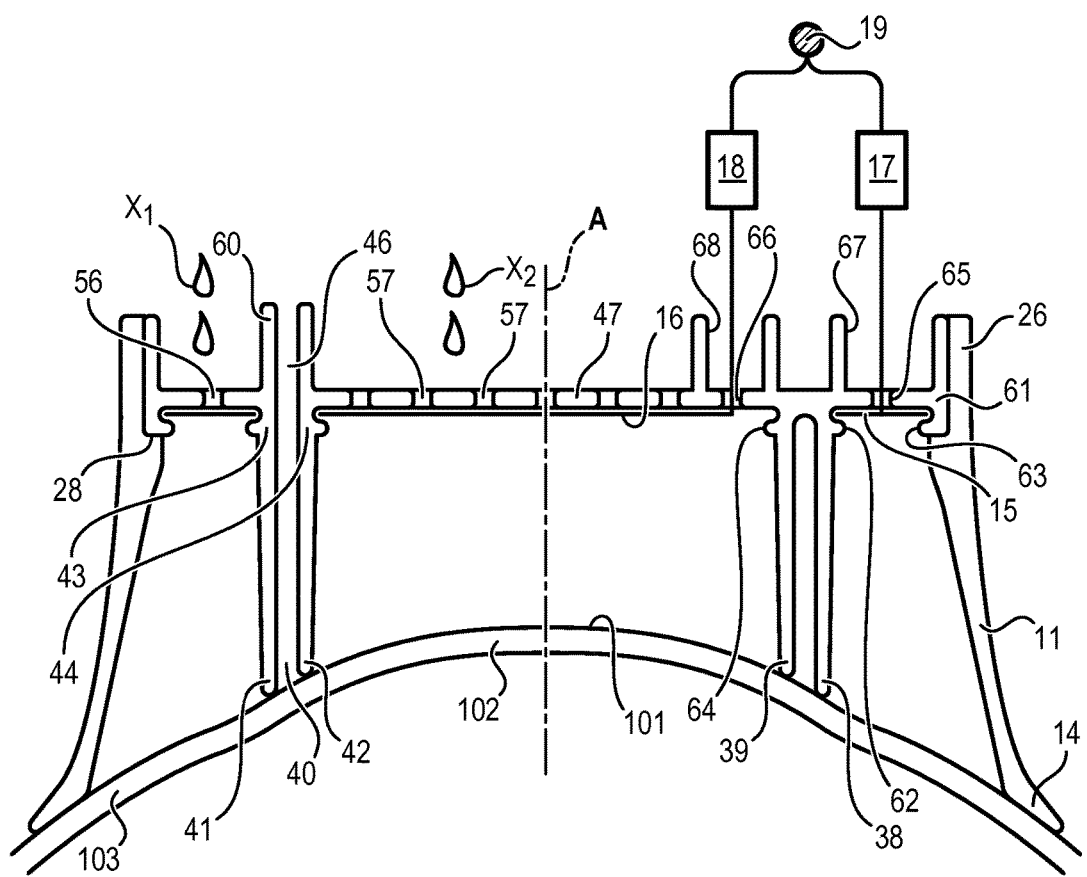
FIG. 9 shows a schematic view of an ocular iontophoresis device according to a sixth embodiment of the invention.

Now referring to FIG. 9, the support surface 47 is integral with first and second separating walls 38, 39.

The support surface 47 is disk-shaped and extends perpendicularly to the longitudinal axis A at the proximal ends 43, 44 of first and second separating walls 38, 39 for closing the suction ring 40 and first and second chambers 21, 22.

The support surface 47 receives the suction opening 46 configured for applying a light vacuum on the ocular surface 101, when the device 10 is positioned on the ocular surface 101. The suction opening 46 is surrounded by a wall 60 extending from the second face of the support surface 47 along first and second separating walls 38, 39.

The support surface 47 comprises for example an annular skirt 61 arranged peripherally and extending along the longitudinal direction in both ways. The annular skirt 61 cooperates with a shoulder 28 arranged at the proximal end 26 of the body wall 11, and configured for stopping a translation of the support surface 47 along the longitudinal direction towards the distal end 14 of the body wall 11.

The annular skirt 61 is preferably made of substantially rigid polymer material. Such a rigid polymer material is for example polymethyl methacrylate (PMMA), polystyrene (PS), acrylonitrile-butadiene-styrene (ABS), polyethylene (PE), polypropylene (PP), polyamide (PA), polycarbonate (PC), or polyurethane (PUR).

The annular skirt 61 can extend more or less towards distal ends 41, 42 of first and second separating walls 38, 39 for adjusting the flexibility of the distal end 14 of the body wall 11. Such an adjustment ensures for example the elastic deformation of the distal end 14 of the body wall 11 when contacting the ocular surface 101, while reinforcing the portion of the body wall 11 cooperating with the annular skirt 61 that is subject to eyelid pressure.

The support surface 47 also receives first and second electrodes 15, 16. First and second electrodes 15, 16 are preferably arranged on the first face of the support surface 47 that is positioned in front of the distal end 14 of the body wall 11. First and second electrodes 15, 16 are for example grid-shaped. Annular protrusions 62, 63 extending radially to the first separating wall 38 and the annular skirt 61 within the first chamber 21 are provided for holding the first electrode 15, while an annular protrusion 64 extending radially to the second separating wall 39 within the second chamber 22 is provided for holding the second electrode 16, so that first and second grid-shaped electrodes 15, 16 can be snapped on the support surface 47.

First and second electrodes 15, 16 are for example connected to first and second current generators 17, 18, respectively, through openings 65, 66 provided in the support surface 47. Openings 65, 66 are for example surrounded by a wall 67, 68 extending from the second face of the support surface 47 along first and second separating walls 38, 39.

The support surface 47 further comprises first openings 56 leading to the first chamber 21 for filling the first chamber 21 with at least one active substance and second openings 57 leading to the second chamber 22 for filling the second chamber 22 with at least one active substance. First and second openings 56, 57 are also used to evacuate gases generated during the iontophoresis within first and second chambers 21, 22, respectively.

Therefore, as illustrated in FIG. 9, two different active substances $X_1$ and $X_2$ can be advantageously applied to the sclera 103 and the cornea 102, respectively. A first active substance $X_1$ is for example filled in the first chamber 21 for treating the sclera 103, while a second active substance $X_2$ is for example filled in the first chamber 22 for treating the cornea 102. First and second active substances $X_1$ and $X_2$ can therefore be adapted for each ocular tissue 102, 103. Therefore, it is possible with the device 10 to treat simultaneously the cornea 102 and the sclera 103 whilst taking into account intrinsic properties of each ocular tissue 102, 103.

The invention claimed is:

1. An ocular iontophoresis device for delivering at least one active substance to an eyeball, comprising:
   a reservoir configured for receiving the at least one active substance,
   a wall defining a tubular-shaped body arranged along a longitudinal axis, delimitating laterally the reservoir and comprising a circular distal end configured for being positioned on an ocular surface of the eyeball and surrounding a cornea and a part of a sclera of the eyeball,
   a first electrode configured to be positioned in front of the part of the sclera which is surrounded by the wall when the wall is in place on said ocular surface, said first electrode being configured for delivering a first current density to the at least one active substance of the reservoir, the ocular iontophoresis device being characterized in that it further comprises:
   a second electrode configured to be positioned in front of the cornea when the wall is in place on said ocular surface, said second electrode being configured for delivering a second current density to the at least one active substance of the reservoir,
   at least one controller for independently controlling said first electrode and said second electrode, and in that:

the second electrode defines a disk-shaped second surface that is arranged over a central part of the reservoir, the first electrode defining an annular-shaped first surface that is arranged over a peripheral part of the reservoir, said first electrode and said second electrode arranged concentrically to each other, so that the first electrode and the second electrode are respectively positioned in front of part of the sclera and in front of the cornea, when the ocular iontophoresis device is positioned on said ocular surface, wherein the reservoir comprises a separating wall defining a first chamber and a second chamber arranged concentrically to each other, the first chamber receiving the first electrode and the second chamber receiving the second electrode.

2. The ocular iontophoresis device according to claim 1, wherein:

a maximum external diameter of the first electrode is 22 mm, a maximum internal diameter of the first electrode is 12.5 mm, and a maximum diameter of the second electrode is 11.5 mm.

3. The ocular iontophoresis device of claim 1, wherein a disk-shaped support surface extends at a proximal end of the separating wall for closing at least the second chamber, and wherein the first electrode and the second electrode are formed directly on the disk-shaped support surface by electroplating or by depositing an ink comprising an electrically conductive material using a technic of pad-printing.

4. The ocular iontophoresis device of claim 1, wherein a disk-shaped support surface extends at a proximal end of the separating wall for closing at least the second chamber and comprises a suction opening leading to the second chamber for applying a vacuum on the cornea when the ocular iontophoresis device is positioned on said ocular surface.

5. The ocular iontophoresis device of claim 1, further comprising a grid arranged within the second chamber and configured for maintaining an elastic deformation of the cornea, when the ocular iontophoresis device is positioned on said ocular surface.

6. The ocular iontophoresis device of claim 1, wherein the first electrode and the second electrode have a distance greater than 4 mm from a distal end of the wall defining the reservoir.

7. An ocular iontophoresis device for delivering at least one active substance to an eyeball, comprising:

a reservoir configured for receiving the at least one active substance, a wall defining a tubular-shaped body arranged along a longitudinal axis, delimitating laterally the reservoir and comprising a circular distal end configured for being positioned on an ocular surface of the eyeball and surrounding a cornea and a part of a sclera of the eyeball, a first electrode configured to be positioned in front of the part of the sclera which is surrounded by the wall when the wall is in place on said ocular surface, said first electrode being configured for delivering a first current density to the at least one active substance of the reservoir, the ocular iontophoresis device being characterized in that it further comprises:

a second electrode configured to be positioned in front of the cornea when the wall is in place on said ocular surface, said second electrode being configured for delivering a second current density to the at least one active substance of the reservoir, at least one controller for independently controlling said first electrode and said second electrode, and in that:

the second electrode defines a disk-shaped second surface that is arranged over a central part of the reservoir, the first electrode defining an annular-shaped first surface that is arranged over a peripheral part of the reservoir, said first electrode and said second electrode arranged concentrically to each other, so that the first electrode and the second electrode are respectively positioned in front of part of the sclera and in front of the cornea, when the ocular iontophoresis device is positioned on said ocular surface, wherein the reservoir comprises a first separating wall and a second separating wall concentrically arranged to the wall defining the reservoir and defining a suction ring arranged between a first chamber provided in a peripheral part of the reservoir and receiving the first electrode and a second chamber provided in a central part of the reservoir and receiving the second electrode.

8. The ocular iontophoresis device of claim 7, wherein the first separating wall comprises a first proximal end and the second separating wall comprises a second proximal end, wherein the first proximal end and the second proximal end are connected to each other via an annular proximal surface for closing the suction ring, said annular proximal surface including a suction opening leading to the suction ring, said annular suction opening being configured for applying a light vacuum on the ocular surface when the ocular iontophoresis device is positioned on the ocular surface so that the ocular iontophoresis device is immobilized while the eyeball is treated.

9. The ocular iontophoresis device of claim 7, further comprising a disk-shaped support surface positioned at a first proximal end of the first separating wall and at a second proximal end of the second separating wall, wherein the disk-shaped support surface receives the first electrode and the second electrode.

10. The ocular iontophoresis device of claim 9, wherein the first electrode and the second electrode are formed directly on the disk-shaped support surface by printing an ink comprising an electrically conductive material using a technic of pad-printing.

11. The ocular iontophoresis device of claim 10, wherein the first electrode is annular-shaped, and the second electrode is spiral-shaped.

12. The ocular iontophoresis device of claim 9, wherein the first electrode and the second electrode are grid-shaped and positioned on the disk-shaped support surface.

13. The ocular iontophoresis device of claim 12, wherein an annular protrusion extending radially to the second separating wall within the second chamber is provided for holding the second electrode.

14. The ocular iontophoresis device of claim 12, wherein annular protrusions extending within the first chamber radially to the first separating wall and an annular skirt arranged peripherally and perpendicularly to the disk-shaped support surface are provided for holding the first electrode.

15. The ocular iontophoresis device of claim 9, wherein the disk-shaped support surface comprises openings leading to the reservoir for evacuating gases generated during iontophoresis.

16. The ocular iontophoresis device of claim 9, wherein the disk-shaped support surface is integral with the first separating wall and the second separating wall.

17. The ocular iontophoresis device of claim 9, wherein the disk-shaped support surface is provided with an outer wall and an inner wall, wherein the outer wall and the inner wall extend perpendicularly to the disk-shaped support surface wherein the outer wall and the inner wall define a groove aligned with the first chamber, while the inner wall defines a cavity aligned with the second chamber.

18. The ocular iontophoresis device of claim 9, wherein the disk-shaped support surface comprises two independent parts, a first part being positioned in front of the first chamber and receiving the first electrode, and a second part being positioned in front of the second chamber and receiving the second electrode.

19. The ocular iontophoresis device of claim 9, wherein the disk-shaped support surface comprises at least one first opening leading to the first chamber for filling the first chamber with the at least one active substance.

20. The ocular iontophoresis device of claim 9, wherein the disk-shaped support surface comprises at least one second opening leading to the second chamber for filling the second chamber with the at least one active substance.

* * * * *